United States Patent
Hasegawa

(10) Patent No.: US 12,161,736 B2
(45) Date of Patent: Dec. 10, 2024

(54) HYDROPHILIC INORGANIC POWDER AND COSMETIC PREPARATION CONTAINING THE SAME

(71) Applicant: MIYOSHI KASEI, INC., Tokyo (JP)

(72) Inventor: Yukio Hasegawa, Tokyo (JP)

(73) Assignee: MIYOSHI KASEI, INC., Tokyo (JP)

(*) Notice: Subject to any disclaimer, the term of this patent is extended or adjusted under 35 U.S.C. 154(b) by 525 days.

(21) Appl. No.: 17/629,560

(22) PCT Filed: Jul. 25, 2019

(86) PCT No.: PCT/JP2019/029295
§ 371 (c)(1),
(2) Date: Jan. 24, 2022

(87) PCT Pub. No.: WO2021/014656
PCT Pub. Date: Jan. 28, 2021

(65) Prior Publication Data
US 2022/0265524 A1    Aug. 25, 2022

(51) Int. Cl.
*A61K 8/19* (2006.01)
*A61K 8/02* (2006.01)
(Continued)

(52) U.S. Cl.
CPC ............ *A61K 8/0241* (2013.01); *A61K 8/062* (2013.01); *A61K 8/361* (2013.01); *A61K 8/86* (2013.01);
(Continued)

(58) Field of Classification Search
CPC ...... A61K 8/0241; A61K 8/062; A61K 8/361; A61K 8/86; A61K 8/891; A61K 2800/622;
(Continued)

(56) References Cited

U.S. PATENT DOCUMENTS 6,482,441 B1 * 11/2002 Hasegawa .............. A61K 8/894
424/490
8,105,691 B2 * 1/2012 Takeuchi ................. A61Q 1/02
424/490
(Continued)

FOREIGN PATENT DOCUMENTS

CN       101309664 A    11/2008
JP       2002-80748 A    3/2002
(Continued)

OTHER PUBLICATIONS

Google translation of JP2013079264A; 2013:78 pages (Year: 2013).*
(Continued)

*Primary Examiner* — Ernst V Arnold

(57) ABSTRACT

A hydrophilic inorganic powder having excellent self-dispersibility in water or an aqueous solvent, which could not be conventionally achieved, and a cosmetic preparation containing the hydrophilic inorganic powder are provided by combining a hydrophilic surfactant and lipophilic surfactant. There is provided the hydrophilic inorganic powder comprising an inorganic powder as a base material; a hydrophobic-coat that covers the surface of the inorganic powder; and a hydrophilic-coat that covers the hydrophobic-coat, wherein ingredients of the hydrophilic-coat comprises both a hydrophilic surfactant and a lipophilic surfactant, and each of the hydrophilic surfactant and the lipophilic surfactant has a branched alkyl moiety in their molecules, wherein the hydrophilic inorganic powder has self-dispersibility in water or an aqueous solvent.

15 Claims, 1 Drawing Sheet

(51) Int. Cl.

| | |
|---|---|
| *A61K 8/06* | (2006.01) |
| *A61K 8/36* | (2006.01) |
| *A61K 8/86* | (2006.01) |
| *A61K 8/891* | (2006.01) |
| *A61Q 1/06* | (2006.01) |
| *A61Q 1/12* | (2006.01) |
| *A61Q 5/12* | (2006.01) |
| *A61Q 15/00* | (2006.01) |

(52) U.S. Cl.
CPC ............... *A61K 8/891* (2013.01); *A61Q 1/06* (2013.01); *A61Q 1/12* (2013.01); *A61Q 5/12* (2013.01); *A61Q 15/00* (2013.01); *A61K 2800/622* (2013.01); *A61K 2800/623* (2013.01); *A61K 2800/624* (2013.01)

(58) Field of Classification Search
CPC ........ A61K 2800/623; A61K 2800/624; A61K 2800/10; A61K 2800/43; A61K 8/25; A61K 8/26; A61K 8/27; A61K 8/37; A61K 8/553; A61K 8/63; A61K 2800/612; A61K 8/4973; A61K 2800/614; A61K 2800/651; A61K 8/29; A61K 8/44; A61K 8/585; A61K 8/39; A61K 8/19; A61Q 1/06; A61Q 1/12; A61Q 5/12; A61Q 15/00; A61Q 1/02; A61Q 5/06; A61Q 17/04; A61Q 19/00; A61Q 1/10
See application file for complete search history.

(56) References Cited

U.S. PATENT DOCUMENTS

| | | |
|---|---|---|
| 8,137,659 B2 | 3/2012 | Kessell |
| 8,420,066 B2 | 4/2013 | Inomata et al. |
| 2006/0013843 A1 | 1/2006 | Shimizu et al. |
| 2008/0044483 A1 | 2/2008 | Kessell |
| 2009/0142383 A1 | 6/2009 | Inomata et al. |
| 2009/0263660 A1 | 10/2009 | Takeuchi et al. |

FOREIGN PATENT DOCUMENTS

| | | | | |
|---|---|---|---|---|
| JP | 4157039 B2 | 9/2008 | | |
| JP | 2012-219028 A | 11/2012 | | |
| JP | 2013-71920 A | 4/2013 | | |
| JP | 2013079264 A | * 5/2013 | ............... | A61K 8/11 |
| JP | 2015-10095 A | 1/2015 | | |
| JP | 2016-117698 A | 6/2016 | | |
| JP | 2016-222589 A | 12/2016 | | |
| JP | 2017-81848 A | 5/2017 | | |
| WO | 2007/007521 A1 | 1/2007 | | |

OTHER PUBLICATIONS

Extended (Supplementary) Search Report dated Apr. 6, 2023, issued in counterpart EP Application No. 19939005.5. (6 pages).
International Search Report dated Oct. 8, 2019, issued in counterpart International Application No. PCT/JP2019/029295. (2 pages).
Notification of Transmittal of Translation of the International Preliminary Report on Patentability (Form PCT/IB/338) issued in counterpart International Application No. PCT/JP2019/029295 mailed Feb. 3, 2022 with Forms PCT/IB/373 and PCT/ISA/237. (8 pages).
Office Action dated Oct. 17, 2023, issued in counterpart CN Application No. 201980098755.0, with English Translation. (12 pages).

* cited by examiner

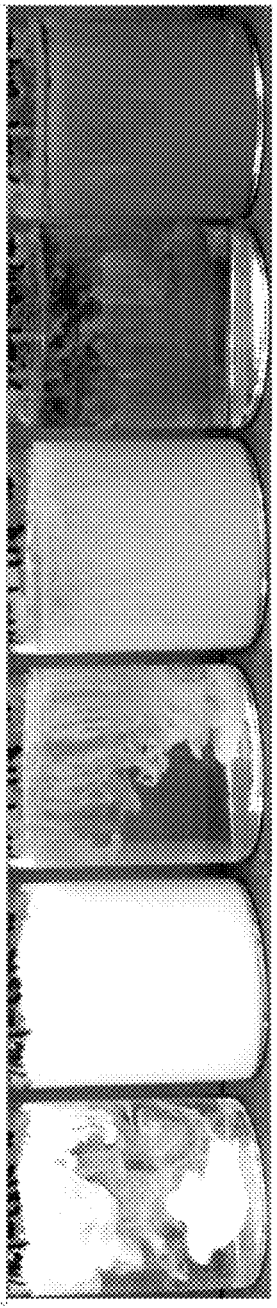
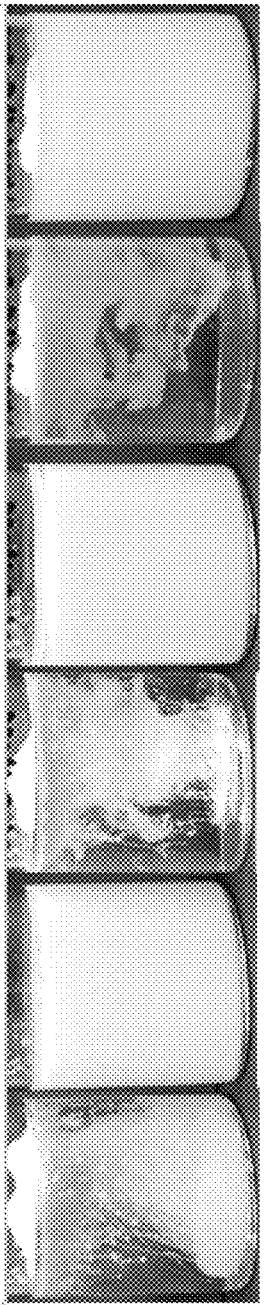

HYDROPHILIC INORGANIC POWDER AND COSMETIC PREPARATION CONTAINING THE SAME

FIELD

The present invention relates to a hydrophilic inorganic powder and cosmetic preparation containing the same.

BACKGROUND

Cosmetic preparations contain pigments and ultraviolet diffusers using zinc oxide, titanium oxide, etc., as a base material. There is demand for containing these pigments and ultraviolet diffusers in the water layer of emulsion cosmetics, however, since zinc oxide and titanium oxide themselves exert potent aggregation property and provide a powdery feel and physical stimulation to the skin, surface treatment is generally performed.

When the demand for containing zinc oxide in the water layer is taken into account, it is considered that the surface of the zinc oxide is coated with a hydrophilizing agent (such as silica), however, the zinc oxide having a silica surface-coat is degraded by acids and alkalis contained in the cosmetics and zinc ions are released (See PTL 1). Therefore, in PTL 1, in first, a hydrophobic first-coat is formed on the surface of zinc oxide using a hydrophobing agent (octyltriethoxysilane) and, subsequently, a hydrophilic second-coat is formed using a surfactant (emulsifier: PEG-11 methyl ether dimethicone) (see PTL 1). PTL 2 discloses a similar technology in which, in first, titanium dioxide is subjected to hydrophobing treatment using sodium stearate and, subsequently, subjected to hydrophilizing treatment using isodecyl alcohol 6-ethoxylate and cetyl alcohol 10-ethoxylate.
[Patent Literature 1 (PTL 1)]
  Japanese Patent Kokai Publication No. JP2016-222589A
[Patent Literature 2 (PTL 2)]
  Japanese Patent No. 4157039

SUMMARY

The following analysis was made from the point of view of the present invention. Each disclosure of PTLs is incorporated herein in its entirety by reference thereto.

As disclosed in PTLs 1 and 2, a combination of the hydrophobing agent and hydrophilizing agent can be variously selected, however, there is a problem that some combinations cannot achieve the desired properties. Herein, as disclosed in PTL 2, it is considered that a property may be provided by using two types of hydrophilizing agents cooperatively, which cannot be provided by a single hydrophilizing agent, however, there are no findings to be an indication upon selection of a combination of hydrophilizing agents.

Therefore, it is an object of the present invention to provide a technology that contributes to providing a hydrophilic inorganic powder having properties that cannot be achieved with a single hydrophilizing agent, by using two types of hydrophilizing agents cooperatively and a cosmetic preparation containing the hydrophilic inorganic powder.

Solution to Problem

According to a first aspect of the present invention, there is provided a hydrophilic inorganic powder, comprising: an inorganic powder as a base material; a hydrophobic-coat that covers the surface of the inorganic powder; and a hydrophilic-coat that covers the hydrophobic-coat, wherein ingredients of the hydrophilic-coat comprise both of a hydrophilic surfactant and a lipophilic surfactant, and each of the hydrophilic surfactant and the lipophilic surfactant has a branched alkyl moiety in their molecules wherein the hydrophilic inorganic powder has self-dispersibility in water or an aqueous solvent.

In the first aspect, it is preferable that the hydrophilic-coat is a nonionic surfactant, the hydrophilic surfactant has a branched alkyl moiety of C12 to C20 in its molecule, and the lipophilic surfactant has a branched alkyl moiety of C16 to C30 in its molecule.

In the first aspect, it is preferable that the hydrophilic surfactant is at least one selected from the following group A, and the lipophilic surfactant is at least one selected from the following group B,
Group A:
  Polyoxyethylene (10) isostearyl ether;
  Polyoxyethylene (20) glyceryl triisostearate;
  Polyoxyethylene (12) isostearate;
  Polyoxyethylene (8) glyceryl isostearate;
  Polyoxyethylene (10) isocetyl ether; and
  Polyoxyethylene (5) isostearyl ether;
Group B:
  Polyglyceryl (2) diisostearate;
  Sorbitan sesquiisostearate; and
  Polyoxyethylene (5) phytosterol.

In the first aspect, it is preferable that the hydrophilic surfactant is polyoxyethylene (10) isostearyl ether.

In the first aspect, it is preferable that the ingredients of the hydrophobic-coat comprise at least one selected from dimethylpolysiloxane, disodium cocoyl glutamate, methyl hydrogen polysiloxane, stearic acid, silicone, and monoisostearyl sebacate.

According to a second aspect of the present invention, there is provided a cosmetic preparation containing the hydrophilic inorganic powder.

According to each aspect of the present invention, there is provided a technology that contributes to providing a hydrophilic inorganic powder having properties that cannot be achieved with a single hydrophilizing agent, by using two types of hydrophilizing agents cooperatively and a cosmetic preparation containing the hydrophilic inorganic powder. Herein, a hydrophilic inorganic powder having self-dispersibility may be referred to as a powder for cosmetics or powdery base material for cosmetics.

BRIEF DESCRIPTION OF DRAWINGS

FIG. 1 shows an example of results of evaluating hydrophilicity and self-dispersibility.

MODES

First, the terms used in the present application will be explained.
[Inorganic Powder]

An inorganic powder is a powder to be a base material of a hydrophilic inorganic powder, and preferably a powder comprising particles of metal oxide or metal hydroxide including at least one of Ti, Zn, Si, Al, Fe, Mg, and Ce. Concretely, they are exemplified by titanium oxide, zinc oxide, silica, aluminum oxide, iron oxide, iron hydroxide, magnesium oxide, and cerium oxide. These inorganic oxide powder particles may be coated with another oxide or hydroxide.

In the present invention, the inorganic powder is not particularly limited as long as it is used for ordinary cosmetics. In other words, the inorganic powders include sericite, natural mica, fired mica, synthetic mica, synthetic sericite, alumina, mica, talc, kaolin, bentonite, smectite, calcium carbonate, magnesium carbonate, magnesium silicate, aluminum silicate, calcium phosphate, anhydrous silicic acid, magnesium oxide, barium sulfate, magnesium aluminometasilicate, iron oxide, chrome oxide, titanium oxide, zinc oxide, cerium oxide, aluminum oxide, magnesium oxide, iron blue, ultramarine blue, calcium carbonate, magnesium carbonate, calcium phosphate, aluminum hydroxide, magnesium sulfate, silicic acid, aluminum magnesium silicate, calcium silicate, barium silicate, strontium silicate, silicon carbide, metal tungstate, magnesium aluminate, magnesium aluminometasilicate, chlorohydroxy aluminum, clay, zeolite, hydroxy apatite, ceramic powder, aluminum nitride, silicon carbide, cobalt titanate, lithium cobalt titanate, cobalt aluminate, inorganic blue pigment, low-order titanium oxide, finely particulate titanium oxide, butterfly-shaped barium sulfate, flower petal-shaped zinc oxide, hexagonal plate-shaped zinc oxide, tetrapod-shaped zinc oxide, finely particulate zinc oxide, titanium oxide-coated mica, titanium oxide-coated mica, titanium oxide-coated silica, titanium oxide-coated synthetic mica, titanium oxide-coated talc, fish scale flake, titanium oxide-coated colored mica, (sodium/calcium) titanium oxide-coated borosilicate, (calcium/aluminum) titanium oxide-coated borosilicate, colcothar-coated mica, colcothar-coated titanium mica, colcothar/black iron oxide-coated titanium mica, carmine-coated titanium mica, carmine/ferric ferrocyanide-coated titanium mica, mango violet, cobalt violet, glass fibers, alumina fibers, etc.

[Hydrophobic-Coat, Hydrophobic Inorganic Powder]

A hydrophobic-coat refers to a hydrophobic coat (also referred to as a hydrophobic first-coat) that that covers the surface of powder, and an inorganic powder covered with a hydrophobic-coat is referred to as a hydrophobic inorganic powder in the present application. Since a hydrophobic-coat is formed with an organic surface treatment agent, it can be said that an ingredient of the hydrophobic-coat is an organic surface treatment agent.

Hydrophobicity refers to a property that, for instance, when 100 cc of purified water is poured into a 200 cc glass beaker, and 0.2 g of powder on a spatula is dropped onto the water surface from a height of 2 cm above the water surface, the water is stirred 50 times with a spatula at a rate of twice a second and then allowed to stand for 30 seconds, powder particles are floating without migrating to the water layer.

[Organic Surface Treatment Agent]

An organic surface treatment agent is an organic treatment agent for coating the surface of an inorganic powder to convert it to have hydrophobicity and is also referred to as a hydrophobing agent. The organic surface treatment agent is exemplified by one or more compounds selected from silicone compounds, alkylsilane, alkyl titanate, polyolefin, acylated amino acid, fatty acid, lecithin, ester oil, fructooligosaccharide, acrylic polymer, and urethane polymer.

As a silicone compound, cyclic methyl hydrogen silicones such as methyl hydrogen polysiloxane (Shin-Etsu Chemical Co., Ltd.: KF99P or KF9901, X-24-9171, X-24-9221, etc.), dimethiconol, single-end type alkoxysilyldimethylpolysiloxane, trimethylsiloxysilicate, and tetrahydrotetramethylcyclotetrasiloxane, acrylic silicones, silicone acrylics, amino modified silicones, carboxy-modified silicone, phosphate-modified silicones, and the like may be used. In addition, as products commercially available from Shin-Etsu Chemical Co., Ltd., KF-9908 (triethoxysilylethyl polydimethylsiloxyethyl dimethicone) and KF-9909 (triethoxysilylethyl polydimethylsiloxyethyl hexyl dimethicone) and the like may also be used. Representative silicone compounds are exemplified by hydrogen dimethicone, dimethylpolysiloxane, methyl hydrogen polysiloxane and the like.

Alkylsilane is exemplified by alkylalkoxysilane. The length of the alkyl chain is exemplified by 1 to 18 carbon atoms, and, concretely, it is exemplified by methyltriethoxysilane, octyltriethoxysilane, octadecyltriethoxysilane, aminopropyltriethoxysilane and the like.

Alkyl titanates (organic titanates) are exemplified by one having a $Ti(OR_1)_4$ structure as its basic structure, in which $R_1$ is independent of each other and is an alkyl group or organic carbonyl group. It is exemplified by isopropyl triisostearoyl titanate (Plenact TTS; Ajinomoto Fine-Techno Co., Inc.) and the like as a commonly available one.

Polyolefins is exemplified by polyolefin resin in which at least one carboxyl group is included in molecules of polyethylene, polypropylene, and the like. For instance, it is exemplified by low molecular weight polyethylene having a molecular weight of 500 to 40,000 and a melting point of 40 degrees Celsius or higher, as disclosed in Japanese Patent Kokai Publication No. JP-Show 63-179972, oxidized polyethylene obtained by oxidizing polypropylene, maleated polyethylene, and oxidized polypropylene.

Acylated amino acids are exemplified by an acylated compound of a saturated fatty acid having 12 to 18 carbon atoms and an amino acid. Here, the amino acids include aspartic acid, glutamic acid, alanine, glycine, sarcosine, proline, and hydroxyproline. Also included as the acylated amino acids are any hydrolysate such as peptides derived from a plant like wheat and pea, silk peptides, animal-derived peptides, or the like. A carboxyl group in the amino acids may be free or a salt os such as K, Na, Fe, Zn, Ca, Mg, Al, Zr, Ti, etc. They are exemplified by, for example, disodium stearoyl glutamate.

More concretely, they are exemplified by Amisofts CS-11, CS-22, MS-11, HS-11P, HS-21P, and the like commercially available from Ajinomoto Co., Inc., Soypon SLP, Soypon SCA, and Alanon AMP commercially available from Kawaken Fine Chemicals Co., Ltd., SEPILIFT DPHP, and the like, commercially available from French company SEPPIC, and Sarcosinate MN, and the like, commercially available from Nikko Chemicals Co., Ltd. These acylated amino acids may be in the form of a composition with a fatty acid. As an acylated lipoamino acid composition, SEPIFEEL ONE (a composition comprising four components: palmitoyl proline, palmitoyl sarcosine, palmitoyl glutamate, and palmitic acid) commercially available from SEPPIC is exemplified.

The fatty acid may be exemplified by a linear or branched saturated or unsaturated fatty acid having 12 to 22 carbon atoms. They are exemplified by fatty acids such as lauryl acid, myristic acid, palmitic acid, stearic acid, oleic acid, linoleic acid, palmitoleic acid, behenic acid, lignoceric acid, 2-ethylhexanoic acid, isotridecanoic acid, isomyristic acid, isopalmitic acid, isostearic acid, isobehenic acid, and the like, or metal salts thereof such as Ca, Mg, Zn, Zr, Al, Ti, and the like.

Lecithin is exemplified by natural lecithin extracted from egg yolk, soybean, corn, rapeseed, sunflower, etc., and glyceride, having a phosphate group, which is hydrogenated lecithin having an iodine value of 15 or less obtained by hydrogenating synthetic lecithin. Examples in the form of salt include water-insoluble hydrogenated lecithin metal salts such as Al, Mg, Ca, Zn, Zr, Ti, and the like.

Ester oil includes ester compounds having a total of 16 or more carbon atoms that can be obtained by reacting one or more types of alcohols having 1 to 36 carbon atoms with one or more types of carboxylic acids having 1 to 36 carbon atoms. Here, a compound having an acid value of 15 or more is preferred. Concretely, they are exemplified by Saracos MIS (isostearyl sebacate), Saracos MOD (octyldodecanol azelate), Saracos 1A (octyldodecanol adipate), Saracos HD (octyldodecanol dimerate) from the Nisshin OilliO Group, Ltd, and the like.

A dextrin fatty acid ester and a fructooligosaccharide ester are esters comprising dextrin or fructooligosaccharide and a fatty acid, or a derivative thereof, and exemplified by Rheopearl KL, Rheopearl MKL, Rheopearl TT, Rheopearl KE, Rheopearl TL, Rheopearl ISK, etc., commercially available from Chiba Flour Milling Co., Ltd.

An acrylic polymer is a copolymer of one or more monomers comprising an acrylic acid or methacrylic acid and an alkyl acrylate, and is exemplified by, as INCI names, (acrylates (C10-30) alkyl acrylate) crosspolymer, (acrylates/beheneth-25 methacrylate) copolymer, and (acrylates/steareth-20 methacrylate) crosspolymer.

A polyurethane polymer is a polymer that has a hydrophilic group moiety of a polyurethane structure and a hydrophobic moiety in its molecule. It is exemplified by, as INCI names, (PEG-240/decyltetradeceth-20/HDI) copolymer (ADEKA NOL GT-700: ADEKA Corporation), bis-stearyl PEG/PPG-8/6 (SMDI/PEG-400) copolymer (AQUPEC HU C2002: Sumitomo Seika Chemicals Co., Ltd.), and the like.

[Hydrophobic Inorganic Powder (Summary)]

As described, the hydrophobic inorganic powder can be prepared variously depending on the combination of the type of the inorganic powder as a base material and the type of the organic surface treatment agent(s), and any inorganic powder converted to have hydrophobic property by coating its surface with an organic surface treatment agent. Hydrophobic inorganic powders described in detail in the present application are listed as follows, and all of them are commonly available.

Dimethylpolysiloxane-treated hydrophobic pigmentary titanium oxide (product name: SA-TSR-10; Miyoshi Kasei, Inc.)

Dimethylpolysiloxane-treated hydrophobic yellow iron oxide (product name: SA-YHP-10; Miyoshi Kasei, Inc.)

Dimethylpolysiloxane-treated hydrophobic red iron oxide (product name: SA-RHP-10; Miyoshi Kasei, Inc.)

Dimethylpolysiloxane-treated hydrophobic black iron oxide (product name: SA-BHP-10; Miyoshi Kasei, Inc.)

Disodium cocoyl glutamate-treated hydrophobic pigmentary titanium oxide (product name: CAI-TSR-10; Miyoshi Kasei, Inc.)

Disodium cocoyl glutamate-treated hydrophobic yellow iron oxide (product name: CAI-YHP-10; Miyoshi Kasei, Inc.)

Disodium cocoyl glutamate-treated hydrophobic red iron oxide (product name: CAI-RHP-10; Miyoshi Kasei, Inc.)

Disodium cocoyl glutamate-treated hydrophobic black iron oxide (product name: CAI-BHP-10; Miyoshi Kasei, Inc.)

Methyl hydrogen polysiloxane-treated hydrophobic ultra-fine titanium oxide (product name: SI-UT-A55; Miyoshi Kasei, Inc.)

Disodium stearoyl glutamate-treated hydrophobic ultra-fine zinc oxide (product name: NAI-Z-300; Miyoshi Kasei, Inc.)

Stearic acid-treated hydrophobic fine titanium dioxide (product name: MT-100Z; Tayca Corporation)

Silicone-treated hydrophobic pigmentary zinc oxide (product name: MZY-505S; Tayca Corporation)

Dimethylpolysiloxane-treated hydrophobic silica beads (product name: SA-SB-150; Miyoshi Kasei, Inc.)

Monoisostearyl sebacate-treated hydrophobic pearl pigment (product name: HS-Timiron Super Silk MP-1005; Miyoshi Kasei, Inc.)

Dimethicone-treated hydrophobic fine zinc oxide (product name: SA-Micro Zinc Oxide; Miyoshi Kasei, Inc.)

Dimethicone-treated talc (product name: SA-Talc JA-46R; Miyoshi Kasei, Inc.)

Herein, since the hydrophobic inorganic powder is commonly available, the details of hydrophobization treatment will be omitted, however, the hydrophobic inorganic powder can be prepared by referring to, for instance, WO2014/102862. Here, in order to increase self-dispersibility in water, when the hydrophobic inorganic powders are manufactured, it is preferable to perform the hydrophobization treatment so that the surfaces of the particles are uniform in a state as close to that of the primary particles as possible.

[Nonionic Surfactant as a Hydrophilic-Coat]

A hydrophilic-coat refers to a hydrophilic coat covering the surface of powder, and, in the present application, refers to a hydrophilic-coat (also referred to as a hydrophilic second-coat) covering the surface of the hydrophobic inorganic powder. The hydrophobic inorganic powder covered with the hydrophilic-coat is referred to as a hydrophilic inorganic powder. Since the hydrophilic-coat is formed by using a hydrophilic surfactant and a lipophilic surfactant cooperatively, it can be said that ingredients of the hydrophilic-coat are hydrophilic and lipophilic surfactants. In the hydrophilic inorganic powder of the present application, a nonionic surfactant as the hydrophilic-coat is a key ingredient providing self-dispersibility in water or an aqueous solvent.

[Nonionic Surfactant]

A nonionic surfactant refers to a surfactant that is never ionized in water. Basically, the nonionic surfactant refers to a surfactant having a structure in which a hydrophilic moiety and a branched alkyl moiety are ether- or ester-bonded and includes hydrophilic and lipophilic surfactants in the present application. Further, the nonionic surfactant includes a glycerol linkage (glyceride) in which structures having hydrophilic and branched alkyl moieties ether- or ester-bonded are linked by polyoxyethylene glycerin.

[Hydrophilic Moiety]

The hydrophilic moiety refers to a moiety having a structure in which ethylene oxide is polymerized (i.e., polyoxyethylene structure) or a structure in which glycerin is polymerized (i.e., polyglycerin structure). Concretely, the polyoxyethylene structure can be represented by $H-(OCH_2CH_2)_n-$ and is sometimes simply referred to as "POE." It may be also referred to as polyethylene glycol and sometimes referred to as "PEG." Further, the polyglycerin structure can be represented by $H-(OCH_2CHOHCH_2)_n-$ and is sometimes simply referred to as "PG." In the above formulae, "n" refers to the degree of polymerization of ethylene oxide or glycerin and is generally referred to as "number of added moles". For instance, a polyoxyethylene structure having 10 of added moles can be referred to as "POE (10)". Note that the number of added mole is an average value or a peak value, and for instance, POE (10) may contain POE (9) or POE (11). Further, a polyglycerin structure having 5 of added moles can be referred to as "PG (5)".

[Branched Alkyl Moiety (Hydrophobic Moiety)]

A branched alkyl moiety refers to a moiety derived from a branched higher alcohol or a branched higher fatty acid and may also be referred to as a hydrophobic moiety. A branched alkyl moiety derived from a branched higher alcohol, which is linked to a hydrophilic moiety to form an ether, has a structure that can be represented by —O(CH$_2$)$_m$H. Further, a branched alkyl moiety derived from a branched fatty acid, which is linked to a hydrophilic moiety to form an ester, has a structure that can be represented by —OCO(CH$_2$)$_{m-1}$H. Note that "m" in the above formulae corresponds to the number of carbon atoms in the branched alkyl moiety. The number of carbon atoms is also an average value or a peak value. Further, the carbon number of a branched alkyl moiety can also be referred to as, for instance, (C18).

The hydrophobic moiety of the nonionic surfactant, which is the hydrophilic-coat of the present invention, is a branched higher alcohol or a branched higher fatty acid. In the present application, branched structures are classified into monomethyl types, dimethyl types, and multi-branched types, however, any branched structure types may be used as if they are sufficient to provide self-dispersibility to the hydrophobic inorganic powder.

[Hydrophilic Surfactant]

A hydrophilic surfactant refers to a hydrophilic nonionic surfactant having a branched alkyl moiety of 12 to 20 carbon atoms in its molecule. The hydrophilic surfactants of ester-type are exemplified by polyoxyethylene branched higher fatty acid monoester, polyoxyethylene sorbitan branched higher fatty acid ester, polyoxyethylene glycerin branched higher fatty acid ester, polyoxyethylene erythritol branched higher fatty acid ester, polyoxyethylene sucrose branched higher fat ester, polyoxyethylene branched higher fatty acid hardened castor oil ester, and polyglycerin branched higher fatty acid ester. The hydrophilic surfactants of ether-types are exemplified by polyoxyethylene branched higher alcohol ether, polyglycerin branched higher alcohol ether, etc.

The branched alkyl alcohols in the hydrophilic surfactant are exemplified by isododecanol, isomyristyl alcohol, isocetyl alcohol, isostearyl alcohol, and isoeicosanol. The branched fatty acids are exemplified by isododecanoic acid, isomyristic acid, isopalmitic acid, isostearic acid, and isoeicosanoic acid.

Concretely, genreally available hydrophilic surfactants are exemplified by Nonion IST-221 (polyoxyethylene-20 sorbitan isostearate: HLB 15.7), Uniox GT-20IS (polyoxyethylene-20 glyceryl triisostearate: HLB 10.4), Uniox GT-30IS (polyoxyethylene-30 glyceryl triisostearate: HLB 12.3), Uniox GM-81S (polyoxyethylene-8 glyceryl triisostearate: HLB 12.0), Nonion IS-4 (polyoxyethylene-8 isostearate: HLB 11.6), and Nonion IS-6 (polyoxyethylene-12 isostearate: HLB 13.7) from NOF Corporation, Decaglyn 1-ISV (polyglyceryl-10 monoisostearate: HLB 12.0) from Nikko Chemicals Co., Ltd., and Nonion IS-205 (polyoxyethylene (5) isostearyl ether: HLB 9.0), Nonion IS-210 (polyoxyethylene-10 isostearyl ether: HLB 12.4), Nonion IS-215 (polyoxyethylene-15 isostearyl ether: HLB 14.2), Nonion IS-220 (polyoxyethylene-20 isostearyl ether: HLB 15.3), and Nonion OD-220 (polyoxyethylene-20 octyldodecanol ether: HLB 14.9) from NOF Corporation, and the like. Further examples include EMALEX 1605 (polyoxyethylene-5 isocetyl ether: HLB 9.5), EMALEX 1610 (polyoxyethylene-10 isocetyl ether: HLB 12.9), EMALEX 1615 (polyoxyethylene-15 isocetyl ether: HLB 14.6), EMALEX 1805 (polyoxyethylene (5) isostearyl ether: HLB 9.0), EMALEX 1810 (polyoxyethylene-10 isostearyl ether: HLB 12.4), EMALEX 1815 (polyoxyethylene-15 isostearyl ether: HLB 14.2), and EMALEX OD-20 (polyoxyethylene-20 octyldodecyl ether: HLB 14.9) from Nihon Emulsion Co., Ltd, and the like.

Considering the hydrolysis resistance of the nonionic surfactant, the dispersibility and the stability over time of the hydrophilic inorganic powder in an aqueous solvent, it is preferable to use a monoether-type POE branched higher alcohol.

[Lipophilic Surfactant]

A lipophilic surfactant refers to a lipophilic nonionic surfactant having a branched alkyl moiety of 16 to 30 carbon atoms in its molecule. The lipophilic surfactants of ester-types are exemplified by polyoxyethylene branched higher fatty acid monoester, polyoxyethylene branched higher fatty acid sorbitan ester, polyoxyethylene branched higher fatty acid glycerin ester, polyoxyethylene branched higher fatty acid erythritol ester, polyoxyethylene branched higher fatty acid sucrose ester, polyoxyethylene branched higher fatty acid hardened castor oil ester, polyglycerin branched higher fatty acid ester, and the like. The lipophilic surfactants of ether-types are exemplified by polyoxyethylene branched higher alcohol ether, polyglycerin branched higher alcohol ether, etc.

The branched alkyl alcohols in the lipophilic surfactant are exemplified by isopalmityl alcohol, isostearyl alcohol, isoeicosanol, cholesterol, phytosterol, and the like. The branched fatty acids are exemplified by isopalmitic acid, isostearic acid, isoeicosane, and the like.

Concretely, the lipophilic surfactants are exemplified by Nonion IS-202 (polyoxyethylene-2 isostearyl ether: HLB 4.9) from NOF Corporation, EMALEX DISG-2EX (polyglyceryl-2 diisostearate: HLB 4.9) and EMALEX PS-5 (polyoxyethylene-5 phytosterol: HLB 7.0) from Nihon Emulsion Co., Ltd., NIKKOL SS-15V (sorbitan sesquiisostearate: HLB 4.2) from Nikko Chemicals Co., Ltd, and the like.

[HLB]

HLB (Hydrophilic-Lipophilic Balance) is a value indicating the degree of affinity of a surfactant to water and oil. In the present application, the HLB is calculated by the following expression.

HLB=(the molecular mass of the hydrophilic moiety (POE or PG) in the surfactant/the molecular mass of the surfactant)×20

[Hydrophilic Inorganic Powder]

A hydrophilic inorganic powder refers to a powder comprising an inorganic powder as a base material, a hydrophobic-coat that covers the surface of the inorganic powder, and a hydrophilic-coat that covers the hydrophobic-coat. That is, when considering that the inorganic powder is a starting material, the surface of the inorganic powder is initially coated with an organic surface treatment agent to convert it to a hydrophobic inorganic powder, and subsequently coated with a nonionic surfactant (i.e., hydrophilized) to convert it to a hydrophilic inorganic powder. Resulting in that the inorganic powder has double coat of the hydrophobic-coat by means of the organic surface treatment agent and the hydrophilic-coat by means of the nonionic surfactant.

The hydrophilization method is not particularly limited, and in the present application, this can be achieved by using the hydrophilic surfactant and the lipophilic surfactant in combination and mixing them in contact with the hydrophobic inorganic powder. Herein, also considered are a preparation method in which a mixed surfactant is prepared preliminary by mixing the hydrophilic surfactant and the lipophilic surfactant, and a preparation method in which the hydrophilic surfactant and the hydrophobic inorganic powder are initially mixed and subsequently the lipophilic surfactant is gradually added thereto. However, any preparation method may be applied as if a finally obtained hydrophilic inorganic powder has a desired hydrophilicity and self-dispersibility. The mixing method is not particularly limited, and a mixer capable of performing uniform processing may by applied. The mixer is exemplified by a Henschel mixer, ribbon blender, kneader, extruder, disperser mixer, homomixer, bead mill, etc. After the ingredients have been mixed, powder can be obtained by drying the mixture with a hot air dryer, spray dryer, flush dryer, conical dryer or the like.

The mixing ratio of the hydrophilic surfactant (A) and the lipophilic surfactant (B) is (A)/(B)=100.0/0.05 to 100/40.0 (wt %). It is preferably 100.0/0.1 to 100/35.0 (wt %). More preferably, it is 100.0/0.1 to 100/30.0 (wt %). If the amount of the lipophilic surfactant is less than 0.05 (wt %), the dispersibility in an aqueous solvent tends to decrease, and if it is more than 40, a hydrophilization treatment may not achieve hydrophilicity.

The mixing ratio of the total amount (A+B) of the hydrophilic surfactant (A) and the lipophilic surfactant (B) and the hydrophobic inorganic powder (C) is (A+B)/(C)= 0.1/99.9 to 20.0/80.0 (wt %). It is preferably 0.1/99.9 to 15.0/85.0 (wt %). More preferably, it is 0.1/99.9 to 10.0/10.0 (wt %). It is preferred that the mixed amount of the surfactants as small as possible in an aspect of skin stimulation.

[Water and Aqueous Solvent]

The hydrophilic inorganic powder of the present application has self-dispersibility in water. The water referred to in the present application refers to ion exchange water, distilled water, and the like. Water used in a cosmetic preparation is one which has been subjected to a preservative treatment or a sterilization treatment. The aqueous solvent of the present application refers to liquid containing a water-soluble alcohol as another ingredient.

For example, alcohols including ethanol, polyhydric alcohol, propylene glycol, dipropylene glycol, 1,3-butylene glycol, polyethylene glycol, glycerin, diglycerin, polyglycerin, hexylglycerin, cyclohexylglycerin, trimethylolpropane, xylitol, erythritol, trehalose, sorbitol and the like are exemplified. The mixing ratio between the water and the alcohol is water/alcohol=100/0 to 50/50 (wt %), however, the lower ratio of the alcohol is preferred from an aspect of self-dispersibility of the hydrophilic inorganic powder.

Further, as an intermediate material during the production of a cosmetic preparation, an aqueous dispersion composition containing a high concentration of hydrophilic inorganic powder may be considered. This aqueous dispersion composition, in which water and hydrophilic inorganic powder are dispersed as main ingredients, can be fluid or granules. By using a disperser in the process of producing the dispersion composition, there is usability benefits, such as the dispersion state of the hydrophilic inorganic powder can be adjusted, the powder particles may be prevented from scattering when they are mixed in the cosmetic preparation, and the like.

The aqueous dispersion composition may appropriately contain, as the other ingredients, a surfactant, emollient, ultraviolet absorber, preservative, antioxidant, film-forming agent, thickening agent, dye, pigment, various pharmacological agents, fragrance, etc.

The surfactant may be a nonionic surfactant, in particular polyoxyethylene (10) isostearyl ether, however, it is explicitly differentiated from the surfactant used when the hydrophilic inorganic powder is prepared (the one used in the present invention).

The thickening agent may be added for the purpose of stably dispersing the hydrophilic inorganic powder in the aqueous dispersion composition over a long period of time, i.e., ensuring storage stability. In other words, depending on the type of the inorganic powder and on the difference in the specific gravity between the hydrophilic inorganic powder and the water or the aqueous solvent, floating or precipitation of the hydrophilic inorganic powder, or syneresis may occur. Here, adding a thickening agent to the water or the aqueous solvent can suppress the floating or precipitation of the hydrophilic inorganic powder.

The thickening agents are exemplified by sodium hyaluronate, cationic sodium hyaluronate, polymer and copolymer comprising acryloyldimethyl taurate and its salt as the constitutional units, polyvinylpyrrolidone and the like. Concretely, exemplified are (sodium acrylates/acryloyldimethyl taurate/dimethylacrylamide) crosspolymer (product name: SEPIMAX ZEN; Seiwa Kasei Co., Ltd.), polyacrylate crosspolymer-6 (product name: SEPINOV P88; Seiwa Kasei Co., Ltd.), (hydroxyethyl acrylate/sodium acryloyldimethyl taurate) copolymer (product name: SEPINOV EMT 10; Seiwa Kasei Co., Ltd.), polyvinylpyrrolidone (product name: Luviskol K 17, Luviskol K 30, Luviskol K 90; BASF Japan Ltd.), mixture of (PEG-240/bis-decyltetradeceth-20/ HDI) copolymer/potassium laurate/butylene glycol/water (ADEKA NOL GT-730: ADEKA Corporation), mixture of polyurethane-59/butylene glycol/water (ADEKA NOL GT-930: ADEKA Corporation), trideceth-6 (Avalure Flex-6 CC Polymer; The Lubrizol Corporation), xanthan gum (Keltrol CG-T; Sansho Co., Ltd.), gellan gum (Kelcogel, Kelcogel HM; DSP Gokyo Food & Chemical Co., Ltd.), sodium magnesium silicate (product name: OVEIL ER (Osaka Gas Chemicals Co., Ltd.)), bentonite (product name: OVEIL BR (Osaka Gas Chemicals Co., Ltd.)) and the like.

[Cosmetic Preparation]

Cosmetic preparations include makeup cosmetics, skin care cosmetics, hair cosmetics, and the like. The makeup cosmetics are exemplified by makeup base, oshiroi face powder (water-based and oil-based), powder foundation, liquid foundation, W/O emulsified foundation, oil-based foundation, oil-based solid foundation, stick foundation, pressed powder, face powder, whitening face powder, lipstick, lipstick top coat, lip gloss, concealer, blusher, eyeshadow (water-based and oil-based), eyebrow cosmetics, eyeliner, mascara, water-based nail enamel, oil-based nail enamel, emulsion nail enamel, nail enamel top coat, nail enamel base coat, and the like. The skin care cosmetics are exemplified by emollient cream, cold cream, skin whitening cream, milky lotion, lotion, beauty essence serum, facial mask, carmine lotion, liquid face wash, facial cleansing foam, facial cleansing cream, facial cleansing powder, makeup remover, body gloss, sunscreen or tanning cream/ lotion, water-based sunscreen lotion, O/W sunscreen cosmetics, and the like. The hair cosmetics are exemplified by hair gloss, hair cream, hair shampoo, hair conditioner, hair dye, hair brushing agent, hair treatment agent, and the like. The antiperspirants are exemplified by cream or lotion, powder, spray-type deodorant products, and the like. In the present application, the cosmetic preparations also comprise milky lotion, soap, bathing agent, perfume, and the like.

EXAMPLES

The present invention will be described in detail with reference to suitable examples and comparative examples corresponding to the examples. It should be noted that the present invention is not limited to the following examples, and corrections, modifications, applications (including partial ones) and combinations thereof are possible without departing from the technical concept of the present invention found in the following examples.

[Evaluation of the Hydrophilicity and the Self-Dispersibility of the Hydrophilic Inorganic Powder]

First, the hydrophilic inorganic powders described in Examples 1 to 17 and Comparative Examples 1 to 7 were prepared and evaluated for their hydrophilicity and self-dispersibility.

Example 1

81.6 g of polyoxyethylene (10) isostearyl ether (Nonion IS-210) and 20.4 g of polyglyceryl (2) diisostearate (EMALEX DISG-2EX) were put into 800 g of ion exchange water and dissolved at 60 degrees Celsius. After this cloudy solution were added to 5 kg of dimethylpolysiloxane-treated hydrophobic pigmentary titanium oxide (product name: SA-TSR-10; Miyoshi Kasei, Inc.), they were mixed for 30 minutes using a kneader mixer, then stirred under vacuum heating for removing the ion exchange water, so as to obtain the powder of Example 1

Example 2

182 g of polyoxyethylene (10) isostearyl ether (Nonion IS-210) and 26 g of polyglyceryl (2) diisostearate (EMALEX DISG-2EX) were put into 2 kg of ion exchange water and dissolved at 60 degrees Celsius. This solution was added to 5 kg of dimethylpolysiloxane-treated hydrophobic yellow iron oxide (product name: SA-YHP-10; Miyoshi Kasei, Inc.), and they were treated like as Example 1, so as to obtain the powder of Example 2.

Example 3

182 g of polyoxyethylene (10) isostearyl ether (Nonion IS-210) and 26 g of polyglyceryl (2) diisostearate (EMALEX DISG-2EX) were put into 1.75 kg of ion exchange water and dissolved at 60 degrees Celsius. This solution was added to 5 kg of dimethylpolysiloxane-treated hydrophobic red iron oxide (product name: SA-RHP-10; Miyoshi Kasei, Inc.), and they were treated like as Example 1, so as to obtain the powder of Example 3.

Example 4

125.8 g of polyoxyethylene (10) isostearyl ether (Nonion IS-210) and 25.8 g of polyglyceryl (2) diisostearate (EMALEX DISG-2EX) were put into 900 g of ion exchange water and dissolved at 60 degrees Celsius. This solution was added to 5 kg of dimethylpolysiloxane-treated hydrophobic black iron oxide (product name: SA-BHP-10; Miyoshi Kasei, Inc.), and they were treated like as Example 1, so as to obtain the powder of Example 4.

Example 5

81.6 g of polyoxyethylene (20) glyceryl triisostearate (Uniox GT-20IS) and 20.4 g of sorbitan sesquiisostearate (NIKKOL SS-15V) were put into 250 g of ion exchange water and dissolved. This cloudy solution and 5 kg of disodium cocoyl glutamate-treated hydrophobic pigmentary titanium oxide (product name: CAI-TSR-10; Miyoshi Kasei, Inc.) were put into a heater Henschel and stirred for 30 minutes. Heating vapor was passed through the jacket of the heater Henschel, and the mixture was stirred while being heated so as to remove the ion exchange water. The mixture was atomized using an atomizer so as to obtain the powder of Example 5.

Example 6

182 g of polyoxyethylene (20) glyceryl triisostearate (Uniox GT-20IS) and 26 g of sorbitan sesquiisostearate (NIKKOL SS-15V) were put into 400 g of ion exchange water and dissolved. This solution was added to 5 kg of disodium cocoyl glutamate-treated hydrophobic yellow iron oxide (product name: CAI-YHP-10; Miyoshi Kasei, Inc.), and they were treated like as Example 5, so as to obtain the powder of Example 6.

Example 7

182 g of polyoxyethylene (20) glyceryl triisostearate (Uniox GT-20IS) and 26 g of polyoxyethylene (5) phytosterol (EMALEX PS-5) were put into 400 g of ion exchange water and dissolved. This solution was added to 5 kg of disodium cocoyl glutamate-treated hydrophobic red iron oxide (product name: CAI-RHP-10; Miyoshi Kasei, Inc.), and they were treated like as Example 5, so as to obtain the powder of Example 7.

Example 8

129.2 g of polyoxyethylene (20) glyceryl triisostearate (Uniox GT-20IS) and 25.8 g of polyglyceryl (2) diisostearate (EMALEX DISG-2EX) were put into 400 g of ion exchange water and dissolved. This solution was added to 5 kg of disodium cocoyl glutamate-treated hydrophobic black iron oxide (product name: CAI-BHP-10; Miyoshi Kasei, Inc.), and they were treated like as Example 5, so as to obtain the powder of Example 8.

Example 9

158.7 g of polyoxyethylene (10) isostearyl ether (Nonion IS-210) and 15.9 g of sorbitan sesquiisostearate (NIKKOL SS-15V) were put into 3 kg of ion exchange water and dissolved at 60 degrees Celsius. A disperser mixer was put into this solution, and while it was stirred, 3 kg of hydrogen dimethicone-treated hydrophobic ultrafine titanium oxide (product name: SI-UT-A55; Miyoshi Kasei, Inc.) was gradually added thereto so as to prepare an aqueous dispersion. This aqueous dispersion was subjected to spray drying using a spray drier having a two-fluid nozzle so as to obtain the powder of Example 9.

Example 10

126 g of polyoxyethylene (10) isostearyl ether (Nonion IS-210) and 32 g of sorbitan sesquiisostearate (NIKKOL SS-15V) were put into 3 kg of ion exchange water and dissolved at 60 degrees Celsius. A disperser mixer was put into this solution, and while it was stirred, 3 kg of disodium stearoyl glutamate-treated hydrophobic ultrafine zinc oxide (product name: NAI-Z-300; Miyoshi Kasei, Inc.) was gradually added thereto so as to prepare an aqueous dispersion. This aqueous dispersion was treated like as Example 9 so as to obtain the powder of Example 10.

Example 11

192.6 g of polyoxyethylene (5) isostearyl ether (Nonion IS-205) and 16 g of polyoxyethylene (5) phytosterol (EMALEX PS-5) were put into 4 kg of ion exchange water and dissolved at 60 degrees Celsius. A disperser mixer was put into this solution, and while it was stirred, 3 kg of stearic acid-treated hydrophobic micro titanium dioxide (product name: MT-100Z; Tayca Corporation) was gradually added thereto so as to prepare an aqueous dispersion. This aqueous dispersion was treated like as Example 9 so as to obtain the powder of Example 11.

Example 12

146 g of polyoxyethylene (5) isostearyl ether (Nonion IS-205) and 21 g of polyoxyethylene (5) phytosterol (EMALEX PS-5) were put into 3.3 kg of ion exchange water and dissolved at 60 degrees Celsius. A disperser mixer was put into this solution, and while it was stirred, 4 kg of hydrogen dimethicone-treated hydrophobic pigmentary zinc oxide (product name: MZY-505S; Tayca Corporation) was treated like as Example 1 so as to obtain the powder of Example 12.

Example 13

125 g of polyoxyethylene (5) isostearyl ether (Nonion IS-210) and 42 g of sorbitan sesquiisostearate (NIKKOL SS-15V) were put into 3.6 kg of ion exchange water and dissolved. A disperser mixer was put into this solution, and while it was stirred, 4 kg of lecithin-treated hydrophobic silica beads (product name: VAI-SB-150; Miyoshi Kasei, Inc.) was treated like as Example 1 so as to obtain the powder of Example 13.

Example 14

The powder of Example 14 was obtained in the same manner as in Example 1, except for replacing the polyglyceryl (2) diisostearate (EMALEX DISG-2EX) of Example 1 with sorbitan sesquiisostearate (NIKKOL SS-15V) and replacing the dimethylpolysiloxane-treated hydrophobic pigmentary titanium oxide with monoisostearyl sebacate-treated hydrophobic pearl pigment (product name: HS-Timiron Super Silk MP-1005; Miyoshi Kasei, Inc.).

Example 15

81.6 g of polyoxyethylene (10) isostearyl ether (Nonion IS-210) and 20.4 g of polyoxyethylene (5) phytosterol (EMALEX PS-5) were put into 800 g of ion exchange water and dissolved at 60 degrees Celsius. This cloudy solution was added to 5 kg of octyltriethoxysilane-treated hydrophobic pigmentary titanium oxide (product name: ALT-TSR-10; Miyoshi Kasei, Inc.), mixed for 30 minutes using a kneader mixer, stirred under vacuum heating so as to remove the ion exchange water. Finally, the powder of Example 15 was obtained.

Example 16

100 g of polyoxyethylene (10) isocetyl ether (Nonion IS-210) and 20 g of polyglyceryl (2) diisostearate (EMALEX DISG-2EX) were put into 1.3 kg of ion exchange water and dissolved at 60 degrees Celsius to obtain a cloudy solution. This cloudy solution was added to 5 kg of dimethicone-treated hydrophobic micro zinc oxide (product name: SA-Micro Zinc Oxide; Miyoshi Kasei, Inc.), and mixed for 30 minutes using a kneader mixer. The mixed product was dried and pulverized using a flush dryer so as to obtain the powder of Example 16.

Example 17

65.3 g of polyoxyethylene (20) glyceryl triisostearate (Uniox GT-20IS) and 16.3 g of polyglyceryl (2) diisostearate (EMALEX DISG-2EX) were put into 1300 g of ion exchange water and dissolved at 60 degrees Celsius. This cloudy solution was added to 4 kg of dimethylpolysiloxane-treated hydrophobic pigmentary titanium oxide (product name: SA-Talc JA-46R; Miyoshi Kasei, Inc.), mixed for 30 minutes using a kneader mixer, and then stirred under vacuum heating so as to remove the ion exchange water. Finally, the powder of Example 17 was obtained.

Comparative Example 1

The powder of Comparative Example 1 was obtained in the same manner as in Example 1, except for replacing the polyoxyethylene (10) isostearyl ether of Example 1 with polyoxyethylene (10) stearyl ether (product name: EMALEX 610 (HLB 14.2)).

Comparative Example 2

81.6 g of polyoxyethylene (9) isodecyl ether (product name: Safetycut ID-1087 (HLB 14.3) Aoki Oil Industrial Co., Ltd.) and 20.4 g of sorbitan sesquiisostearate (NIKKOL SS-15V) were put into 250 g of ion exchange water and dissolved. 5 kg of the disodium cocoyl glutamate-treated hydrophobic pigmentary titanium oxide (product name: CAI-TSR-10; Miyoshi Kasei, Inc.) used in Example 5 was put into a heater Henschel, the solution prepared above was subsequently added thereto, and the mixture was stirred for 30 minutes. Heating vapor was passed through the jacket of the heater Henschel, and the mixture was stirred while being heated to remove the ion exchange water. The mixture was atomized using an atomizer so as to obtain the powder of Comparative Example 2.

Comparative Example 3

182 g of polyoxyethylene (20) glyceryl tristearate (EMALEX GWS-320) and 26 g of polyglyceryl (2) diisostearate (EMALEX DISG-2EX) were put into 250 g of ion exchange water and dissolved. 5 kg of the disodium cocoyl glutamate-treated hydrophobic pigmentary titanium oxide (product name: CAI-YHP-10; Miyoshi Kasei, Inc.) used in Example 6 was put into a heater Henschel, the solution prepared above was subsequently added thereto, and the mixture was stirred for 30 minutes. Heating vapor was passed through the jacket of the heater Henschel, and the mixture was stirred while being heated so as to remove the ion exchange water. The mixture was atomized using an atomizer so as to obtain the powder of Comparative Example 3.

Comparative Example 4

182 g of polyoxyethylene (20) glyceryl tristearate (EMALEX GWS-320) and 26 g of sorbitan sesquiisostearate (NIKKOL SS-15V) were put into 250 g of ion exchange water and dissolved. 5 kg of the disodium cocoyl glutamate-treated hydrophobic pigmentary titanium oxide (product name: CAI-RHP-10; Miyoshi Kasei, Inc.) used in Example 7 was put into a heater Henschel, the solution prepared above was subsequently added thereto, and the mixture was stirred for 30 minutes. Heating vapor was passed through the jacket of the heater Henschel, and the mixture was stirred while being heated so as to remove the ion exchange water. The mixture was atomized using an atomizer so as to obtain the powder of Comparative Example 4.

Comparative Example 5

129.2 g of polyoxyethylene (20) glyceryl tristearate (EMALEX GWS-320) and 25.8 g of sorbitan sesquiisostearate (NIKKOL SS-15V) were put into 250 g of ion exchange water and dissolved. 5 kg of the disodium cocoyl glutamate-treated hydrophobic pigmentary titanium oxide (product name: CAI-BHP-10; Miyoshi Kasei, Inc.) used in Example 8 was put into a heater Henschel, the solution prepared above was subsequently added thereto, and the mixture was stirred for 30 minutes. Heating vapor was passed through the jacket of the heater Henschel, and the mixture was stirred while being heated so as to remove the ion exchange water. The mixture was atomized using an atomizer so as to obtain the powder of Comparative Example 5.

Comparative Example 6

The powder of Comparative Example 6 was obtained in the same manner as in Example 11, except for replacing the polyoxyethylene (10) isostearate of Example 11 with polyoxyethylene (10) stearyl ether (product name: EMALEX 610 (HLB 12.4)).

Comparative Example 7

The powder of Comparative Example 7 was obtained in the same manner as in Example 10, except for replacing the polyoxyethylene (10) isostearyl ether of Example 10 with polyether-modified silicone (product name: KF-6013 (HLB 10.0); Shin-Etsu Chemical Co., Ltd.).

Comparative Example 8

The inorganic powder as a base material for the powder of each of the examples and the comparative examples was prepared as it was for comparative evaluation. Unlike the powders of the other examples and comparative examples, these inorganic powders (untreated) do not have any of hydrophobic- or hydrophilic-coats, and the inorganic powders themselves are exposed, thus they have hydrophilicity.

Herein, the inorganic powder as a base material, the organic surface treatment agent, the hydrophilic surfactant, and the lipophilic surfactant of the powder of each example/comparative example are summarized as follows.

| | Inorganic powder | Organic surface treatment agent | Hydrophilic surfactant | Lipophilic surfactant |
|---|---|---|---|---|
| Example 1 | Pigmentary titanium oxide | Dimethylpolysiloxane | Polyoxyethylene (10) isostearyl ether | Polyglyceryl (2) diisostearate |
| Example 2 | Yellow iron oxide | Dimethylpolysiloxane | Polyoxyethylene (10) isostearyl ether | Polyglyceryl (2) diisostearate |
| Example 3 | Red iron oxide | Dimethylpolysiloxane | Polyoxyethylene (10) isostearyl ether | Polyglyceryl (2) diisostearate |
| Example 4 | Black iron oxide | Dimethylpolysiloxane | Polyoxyethylene (10) isostearyl ether | Polyglyceryl (2) diisostearate |
| Example 5 | Pigmentary titanium oxide | Disodium cocoyl glutamate | Polyoxyethylene (20) glyceryl triisostearate | Sorbitan sesquiisostearate |
| Example 6 | Yellow iron oxide | Disodium cocoyl glutamate | Polyoxyethylene (20) glyceryl triisostearate | Sorbitan sesquiisostearate |
| Example 7 | Red iron oxide | Disodium cocoyl glutamate | Polyoxyethylene (20) glyceryl triisostearate | Polyoxyethylene (5) phytosterol |
| Example 8 | Black iron oxide | Disodium cocoyl glutamate | Polyoxyethylene (20) glyceryl triisostearate | Polyglyceryl (2) diisostearate |
| Example 9 | Ultrafine titanium oxide | Hydrogen dimethicone | Polyoxyethylene (10) isostearyl ether | Sorbitan sesquiisostearate |
| Example 10 | Ultrafine zinc oxide | Disodium stearoyl glutamate | Polyoxyethylene (10) isostearyl ether | Sorbitan sesquiisostearate |
| Example 11 | Micro titanium dioxide | Stearic acid | Polyoxyethylene (5) isostearyl ether | Polyoxyethylene (5) phytosterol |
| Example 12 | Ultrafine zinc oxide | Hydrogen dimethicone | Polyoxyethylene (5) isostearyl ether | Polyoxyethylene (5) phytosterol |
| Example 13 | Silica | Lecithin | Polyoxyethylene (5) isostearyl ether | Sorbitan sesquiisostearate |
| Example 14 | Pearl pigment | Monoisostearyl sebacate | Polyoxyethylene (10) isostearyl ether | Sorbitan sesquiisostearate |
| Example 15 | Pigmentary titanium oxide | Octyltriethoxysilane | Polyoxyethylene (10) isostearyl ether | Polyoxyethylene (5) phytosterol |
| Example 16 | Pigmentary zinc oxide | Dimethylpolysiloxane | Polyoxyethylene (10) isocetyl ether | Polyglyceryl (2) diisostearate |
| Example 17 | Talc | Dimethylpolysiloxane | Polyoxyethylene (20) octyldodecyl ether | Polyglyceryl (2) diisostearate |
| Comparative Example 1 | Pigmentary titanium oxide | Dimethylpolysiloxane | Polyoxyethylene (10) stearyl ether | Polyglyceryl (2) diisostearate |
| Comparative Example 2 | Pigmentary titanium oxide | Disodium cocoyl glutamate | Polyoxyethylene (9) isodecyl ether | Sorbitan sesquiisostearate |

-continued

| | Inorganic powder | Organic surface treatment agent | Hydrophilic surfactant | Lipophilic surfactant |
|---|---|---|---|---|
| Comparative Example 3 | Yellow iron oxide | Disodium cocoyl glutamate | Polyoxyethylene (20) glyceryl tristearate | Polyglyceryl (2) diisostearate |
| Comparative Example 4 | Red iron oxide | Disodium cocoyl glutamate | Polyoxyethylene (20) glyceryl tristearate | Sorbitan sesquiisostearate |
| Comparative Example 5 | Black iron oxide | Disodium cocoyl glutamate | Polyoxyethylene (20) glyceryl tristearate | Sorbitan sesquiisostearate |
| Comparative Example 6 | Micro titanium dioxide | Hydrogen dimethicone | Polyoxyethylene (5) stearyl ether | Polyoxyethylene (5) phytosterol |
| Comparative Example 7 | Ultrafine zinc oxide | Disodium stearoyl glutamate | Polyoxyethylene (10) stearyl ether | Sorbitan sesquiisostearate |

(Method for Evaluating Hydrophilicity and Self-Dispersibility)

Test 1

30 cc of ion exchange water was poured into a 50-cc glass vial, and 0.2 g of powder on a spatula was dropped from a height of 3 cm above the water surface. Then, how the powder particles enter and fall into the water was observed according to the following evaluation criteria. After the powder was dropped on the surface of the water, the liquid was not physically stirred at all, and the way the powder particles naturally diffuse and disperse in the water (i.e., self-dispersibility) was observed.

Test 2

The same evaluation as in Test 1 was performed except for changing the ion exchange water in Test 1 to a solution of ion exchange water/butylene glycol (BG)=6/4 (wt %).

Test 3

The same evaluation as in Test 1 was performed except for changing the ion exchange water in Test 1 to a solution of ion exchange water/glycerin (G)=6/4 (wt %).

(Evaluation Criteria for Hydrophilicity and Self-Dispersibility)

○: 60 seconds after the powder particles self-dispersed (self-diffused) in the water layer, the powder particles diffused throughout the water layer and the liquid became cloudy.

Δ: The powder particles were precipitated in the water layer and the rest floated on the water surface.

x: The powder particles floated on the water surface.

Herein, FIG. 1 shows examples of evaluation of hydrophilicity and self-dispersibility (Examples 1 to 3 and 9 to 11 are all ○) and shows a state immediately after the powder is put into the ion exchange water (left) and a state after 60 seconds (right).

TABLE 1

| | Test 1: Ion exchange water | | Test 2: Ion exchange water/BG | | Test 3: Ion exchange water/G | |
|---|---|---|---|---|---|---|
| | Hydrophilized | Untreated (Comparative Example 8) | Hydrophilized | Untreated (Comparative Example 8) | Hydrophilized | Untreated (Comparative Example 8) |
| Example 1 | ○ | x | ○ | x | ○ | x |
| Example 2 | ○ | x | ○ | x | ○ | x |
| Example 3 | ○ | x | ○ | x | ○ | x |
| Example 4 | ○ | x | ○ | x | ○ | x |
| Example 5 | ○ | x | ○ | x | ○ | x |
| Example 6 | ○ | x | ○ | x | ○ | x |
| Example 7 | ○ | x | ○ | x | ○ | x |
| Example 8 | ○ | x | ○ | x | ○ | x |
| Example 9 | ○ | x | ○ | x | ○ | x |
| Example 10 | ○ | x | ○ | x | ○ | x |
| Example 11 | ○ | x | ○ | x | ○ | x |
| Example 12 | ○ | x | ○ | x | ○ | x |
| Example 13 | ○ | x | ○ | x | ○ | x |
| Example 14 | ○ | x | ○ | x | ○ | x |
| Example 15 | ○ | x | ○ | x | ○ | x |
| Example 16 | ○ | x | ○ | x | ○ | x |
| Example 17 | ○ | x | ○ | x | ○ | x |
| Comparative Example 1 | x | — | x | — | x | — |
| Comparative Example 2 | x | — | x | — | x | — |
| Comparative Example 3 | x | — | x | — | x | — |
| Comparative Example 4 | x | — | x | — | x | — |
| Comparative Example 5 | x | — | x | — | x | — |
| Comparative Example 6 | Δ | — | Δ | — | Δ | — |
| Comparative Example 7 | Δ | — | Δ | — | Δ | — |

(Discussion for the Evaluation Results (1))

The evaluation results of Example 1 and Comparative Example 8 show that hydrophilicity and self-dispersibility are apparently improved by both hydrophobing and hydrophilizing the inorganic powder as a base material. Particularly, as shown in Table 1, the powders of Examples 1 to 17 have significant utility in terms of the property of naturally diffusing and dispersing (i.e., self-dispersibility) after being dropped in ion exchange water without being physically stirred. More concretely, it can be said that the powders of Examples 1 to 17 self-disperse and is uniformly mixed in an aqueous solvent within several tens of seconds (within 60 seconds at most) after being dropped therein.

(Discussion for the Evaluation Results (2))

The evaluation results of Example 1 and Comparative Example 1 show that a case of using polyoxyethylene (10) isostearyl ether as the hydrophilic surfactant (Example 1: ○) achieves better hydrophilicity and self-dispersibility than a case of using polyoxyethylene (10) stearyl ether as the surfactant (Comparative Example 1: x). The evaluation results of Example 9 and Comparative Example 6 indicate the same.

(Discussion for the Evaluation Results (3))

The evaluation results of Examples 1, 9, and 10 show that a case of using polyoxyethylene (10) isostearyl ether as the hydrophilic surfactant achieves good hydrophilicity and self-dispersibility independently of the organic surface treatment agent.

(Discussion for the Evaluation Results (4))

The evaluation results of Examples 1, 9, and 10 show that a case of using polyoxyethylene (10) isostearyl ether as the hydrophilic surfactant achieves good hydrophilicity and self-dispersibility independently of the lipophilic surfactant.

[Evaluation of the Usability, Cosmetic Effects, and Cosmetic Durability of O/W Emulsified Foundation (1)]

O/W emulsified foundations of Example 18 and Comparative Example 9 containing the following ingredients were prepared, and the usability, cosmetic effects, and cosmetic durability of each O/W emulsified foundation were evaluated.

(Method for Preparing the O/W Emulsified Foundations)

A: Oil layer ingredients were dispersed and mixed well.
B: Water layer ingredients were dispersed and mixed well.
C: After A was added to B, the mixture was emulsified with a homomixer to obtain an O/W emulsified foundation.

(Method for Evaluating Usability, Cosmetic Effects, and Cosmetic Durability)

25 expert panelists were asked to use each O/W foundation for a day and score the foundations using five grades shown below. Then, usability, cosmetic effects, and cosmetic durability were evaluated according to the average scores thereof. The usability was evaluated from the viewpoints of lubricity, non-stickiness, and comfortableness. The cosmetic effects were evaluated from the viewpoints of powderiness, application evenness, cosmetic film uniformity, and natural luster. Further, the cosmetic durability was evaluated from the viewpoints of generation of skin color dullness, greasy skin texture, and powder patchiness occur with the passage of time.

(Evaluation Criteria)

Evaluation result: Score
Very good: 5
Good: 4
Fair: 3
Somewhat poor: 2
Very poor: 1

TABLE 2

| | Ingredients | Example 18 | Comparative Example 9 |
|---|---|---|---|
| Oil layer ingredients | Isohexadecane | 13.0 (wt %) | 13.0 (wt %) |
| | Glyceryl tri-2-ethylhexanoate | 5.5 | 5.5 |
| | 2-ethylhexyl p-methoxycinnamate | 5.0 | 5.0 |
| | Behenyl alcohol | 1.0 | 1.0 |
| | Dibutylhydroxytoluene | 0.05 | 0.05 |
| Aqueous layer ingredients | Powder of Example 1 (titanium oxide) | 8.0 | — |
| | Powder of Example 2 (yellow iron oxide) | 3.1 | — |
| | Powder of Example 3 (red iron oxide) | 2.1 | — |
| | Powder of Example 4 (black iron oxide) | 0.2 | — |
| | Powder of Comparative Example 2 (titanium oxide) | — | 8.0 |
| | Powder of Comparative Example 3 (yellow iron oxide) | — | 3.1 |
| | Powder of Comparative Example 4 (red iron oxide) | — | 2.1 |
| | Powder of Comparative Example 5 (black iron oxide) | — | 0.2 |
| | BG | 5.0 | 5.0 |
| | Ethanol | 5.0 | 5.0 |
| | Carbomer | 0.2 | 0.2 |
| | Triethanolamine | 0.1 | 0.1 |
| | Phenoxyethanol | 0.5 | 0.5 |
| | Ion exchange water | Remainder | Remainder |
| Evaluation results | Usability | 4.5 | 3.0 |
| | Cosmetic effects | 4.8 | 2.7 |
| | Cosmetic durability | 4.3 | 2.6 |

The evaluation results of Example 18 show that the powders of Examples 1 to 4 can achieve good usability, cosmetic effects, and cosmetic durability when prepared as an O/W emulsified foundation. On the other hand, the evaluation results of Comparative Example 9 show that, when prepared as an O/W emulsified foundation, the powders of Comparative Examples 2 to 5 have poorer usability, cosmetic effects, and cosmetic durability than the powders of Examples 1 to 4.

[Evaluation of the Usability, Cosmetic Effects, and Cosmetic Durability of O/W Emulsified Foundation (2)]

O/W emulsified foundations having ingredients shown in Example 19 and Comparative Examples 10 and 11 below were prepared, and the usability, cosmetic effects, and cosmetic durability of each O/W emulsified foundation were evaluated.

(Producing and Evaluation Methods)

The producing and evaluation methods are the same as in Example 18, however, a significant difference is that Comparative Example 10 contains as its water layer ingredients dimethylpolysiloxane-treated hydrophobic pigmentary titanium oxide, dimethylpolysiloxane-treated hydrophobic yellow iron oxide, dimethylpolysiloxane-treated hydrophobic red iron oxide and dimethylpolysiloxane-treated hydrophobic black iron oxide, which correspond to the hydrophobic inorganic powders before the hydrophilization treatment in Examples 1 to 4, respectively.

TABLE 3

| | Ingredients | Example 19 | Comparative Example 10 | Comparative Example 11 |
|---|---|---|---|---|
| Oil layer ingredients | Decamethylcyclopentasiloxane | 11.0 (wt %) | 11.0 (wt %) | 11.0 (wt %) |
| | Isohexadecane | 5.5 | 5.5 | 5.5 |
| | Triethylhexanoin | 5.0 | 5.0 | 5.0 |
| | 2-ethylhexyl p-methoxycinnamate | 8.0 | 8.0 | 8.0 |
| | PEG-9 polydimethylsiloxyethyl dimethicone | 4.0 | 4.0 | 4.0 |
| | Silicone-treated finely particulate zinc oxide | 6.5 | 6.5 | 6.5 |
| | Dimethylpolysiloxane-treated hydrophobic pigmentary titanium oxide | — | 7.5 | — |
| | Dimethylpolysiloxane-treated hydrophobic yellow iron oxide | — | 3.0 | — |
| | Dimethylpolysiloxane-treated hydrophobic red iron oxide | — | 1.2 | — |
| | Dimethylpolysiloxane-treated hydrophobic black iron oxide | — | 0.3 | — |
| Aqueous layer ingredients | Powder of Example 1 (titanium oxide) | 7.5 | — | — |
| | Powder of Example 2 (yellow iron oxide) | 3.0 | — | — |
| | Powder of Example 3 (red iron oxide) | 1.2 | — | — |
| | Powder of Example 4 (black iron oxide) | 0.3 | — | — |
| | Powder of Comparative Example 2 (titanium oxide) | — | — | 7.5 |
| | Powder of Comparative Example 3 (yellow iron oxide) | — | — | 3.0 |
| | Powder of Comparative Example 4 (red iron oxide) | — | — | 1.2 |
| | Powder of Comparative Example 5 (black iron oxide) | — | — | 0.3 |
| | BG | 6.0 | 6.0 | 6.0 |
| | Phenoxyethanol | 0.8 | 0.8 | 0.8 |
| | Ion exchange water | To 100.0 | To 100.0 | To 100.0 |
| Evaluation results | Usability | 4.4 | 3.5 | 2.3 |
| | Cosmetic effects | 4.4 | 3.6 | 2.9 |
| | Cosmetic durability | 4.2 | 4.0 | 2.5 |

The evaluation results of Example 19 show that the powders of Examples 1 to 4 can achieve good usability, cosmetic effects, and cosmetic durability when contained in an O/W emulsified foundation as water layer ingredients (Example 19).

Further, the evaluation results of Comparative Example 10 show that, when contained in an O/W emulsified foundation as oil layer ingredients (Comparative Example 10), hydrophobic inorganic powders before hydrophilization treatment can achieve reasonable usability, cosmetic effects, and cosmetic durability, but the results of Comparative Example 10 are inferior to those of Example 19.

The evaluation results of Comparative Examples 10 and 11 show that the powders of Comparative Examples 2 to 5 have poorer usability, cosmetic effects, and cosmetic durability than the powders before the hydrophilization treatment.

[Evaluation of the Usability, Cosmetic Effects, Cosmetic Durability, and SPF Value of Water-Based Sunscreen Lotion]

Water-based sunscreen lotions having ingredients shown in Example 20 and Comparative Examples 12 and 13 below were prepared, and the usability, cosmetic effects, cosmetic durability, and SPF value of each water-based sunscreen lotion were evaluated.

(Producing Method)

A: Oil layer ingredients were dispersed and mixed well.

B: Water layer ingredients were dispersed and mixed well.

C: After A was added to B, the mixture was emulsified with a homomixer to obtain a water-based sunscreen lotion.

(Evaluation Method)

The in-vitro SPF value was measured as an additional item for each water-based sunscreen lotion. The method for evaluating the other attributes was the same as in the case of the O/W emulsified foundations described above, however, a significant difference is that Comparative Example 12 contains hydrophobic inorganic powders before hydrophilization treatment (which correspond to the hydrophobic inorganic powders before the hydrophilization treatment in Examples 10 and 11) as its water layer ingredients.

TABLE 4

| | Ingredients | Example 20 | Comparative Example 12 | Comparative Example 13 |
|---|---|---|---|---|
| Oil layer ingredients | Decamethylcyclopentasiloxane | 15.0 (wt %) | 15.0 (wt %) | 15.0 (wt %) |
| | Dimethylpolysiloxane (6 cs) | 5.0 | 5.0 | 5.0 |
| | Triethylhexanoin | 6.0 | 6.0 | 6.0 |
| | Methyl hydrogen polysiloxane-treated hydrophobic ultrafine titanium oxide | — | 8.0 | — |
| | Disodium stearoyl glutamate-treated hydrophobic ultrafine zinc oxide | — | 10.0 | — |
| Aqueous layer ingredients | Powder of Example 9 (titanium oxide) | 8.0 | — | — |
| | Powder of Example 10 (zinc oxide) | 10.0 | — | — |
| | Powder of Comparative Example 6 (titanium oxide) | — | — | 8.0 |
| | Powder of Comparative Example 7 (zinc oxide) | — | — | 10.0 |
| | PEG-10 dimethicone | 3.0 | 3.0 | 3.0 |
| | Glyceryl monostearate | 1.5 | 1.5 | 1.5 |
| | BG | 5.0 | 5.0 | 5.0 |
| | Ethanol | 5.0 | 5.0 | 5.0 |
| | Purified water | Remainder | Remainder | Remainder |
| Evaluation results | Usability | 4.5 | 4.0 | 3.5 |
| | Cosmetic effects | 4.4 | 3.9 | 3.5 |
| | Cosmetic durability | 4.2 | 4.0 | 3.3 |
| | In-vitro SPF value | 39.1 | 33.6 | 25.9 |

The results of Table 4 show that the water-based sunscreen lotion containing the powders of Examples 9 and 10 has high ultraviolet shielding ability and excellent usability, cosmetic effects, and cosmetic durability.

[Evaluation of the Usability, Cosmetic Effects, Cosmetic Durability, and SPF Value of O/W Sunscreen Cosmetic Preparations (1)]

O/W sunscreen cosmetic preparations having ingredients shown in Example 21 and Comparative Example 14 below were prepared, and the usability, cosmetic effects, cosmetic durability, and SPF value of each O/W sunscreen cosmetic preparation were evaluated.

(Producing and Evaluation Methods)

The methods for producing and evaluating the O/W sunscreen cosmetic preparations were the same as those for the water-based sunscreen lotions described above.

TABLE 5

| | Ingredients | Example 21 | Comparative Example 14 |
|---|---|---|---|
| Oil layer ingredients | Isododecane | 8.0 | 8.0 |
| | Glyceryl octanoate | 4.0 | 4.0 |
| | Dimethylpolysiloxane (10 cs) | 3.0 | 3.0 |
| | Cetostearyl alcohol | 1.0 | 1.0 |
| | 2-ethylhexyl p-methoxycinnamate | 5.0 | 5.0 |
| Aqueous layer ingredients | Powder of Example 10 (zinc oxide) | 12.0 | — |
| | Powder of Comparative Example 7 (zinc oxide) | — | 12.0 |
| | PEG-80 hydrogenated castor oil | 1.0 | 1.0 |
| | Sodium acrylate/acryloyldimethyl taurate copolymer | 0.2 | 0.2 |
| | Xanthan gum | 0.1 | 0.1 |
| | Phenoxyethanol | 0.7 | 0.7 |

TABLE 5-continued

| | Ingredients | Example 21 | Comparative Example 14 |
|---|---|---|---|
| | Glycerin | 5.0 | 5.0 |
| | Ethanol | 5.0 | 5.0 |
| | Purified water | Remainder | Remainder |
| Evaluation results | Usability | 4.8 | 4.0 |
| | Cosmetic effects | 4.5 | 4.0 |
| | Cosmetic durability | 4.2 | 4.0 |
| | In-vitro SPF value | 32.8 | 25.4 |

The results of Table 5 show that the O/W sunscreen cosmetic preparation containing the powder of Example 10 has high ultraviolet shielding ability and excellent usability, cosmetic effects, and cosmetic durability.

[Evaluation of the Usability, Cosmetic Effects, Cosmetic Durability, and SPF Value of O/W Sunscreen Cosmetic Preparations (2)]

O/W sunscreen cosmetic preparations having ingredients shown in Example 22 and Comparative Example 15 below were prepared, and the usability, cosmetic effects, cosmetic durability, and SPF value of each O/W sunscreen cosmetic preparation were evaluated.

(Producing and Evaluation Methods)

The methods for producing and evaluating the O/W sunscreen cosmetic preparations were the same as those for the water-based sunscreen lotions described above.

TABLE 6

| | Ingredients | Example 22 | Comparative Example 15 |
|---|---|---|---|
| Oil layer ingredients | Decamethylcyclopentasiloxane | 10.0 (wt %) | 10.0 (wt %) |
| | Isododecane | 9.0 | 10.0 |
| | Diisopropyl sebacate | 8.0 | 8.0 |
| | PEG-10 dimethicone | 4.0 | 4.0 |

TABLE 6-continued

|  | Ingredients | Example 22 | Comparative Example 15 |
|---|---|---|---|
|  | Diethylamino hydroxybenzoyl hexyl benzoate | 8.0 | 8.0 |
| Aqueous layer ingredients | Powder of Example 9 (titanium oxide) | 5.0 | — |
|  | Powder of Example 10 (zinc oxide) | 10.0 | — |
|  | Powder of Comparative Example 6 (titanium oxide) | — | 5.0 |
|  | Powder of Comparative Example 7 (zinc oxide) | — | 10.0 |
|  | BG | 10.0 | 10.0 |
|  | Erythritol | 2.0 | 2.0 |
|  | Phenoxyethanol | 0.5 | 0.5 |
|  | Purified water | Remainder | Remainder |
| Evaluation results | Usability | 4.5 | 4.2 |
|  | Cosmetic effects | 4.3 | 3.9 |
|  | Cosmetic durability | 4.3 | 3.9 |
|  | In-vitro SPF value | 45.3 | 38.8 |

The results of Table 6 show that the O/W sunscreen cosmetic preparation containing the powders of Examples 9 and 10 has high ultraviolet shielding ability and excellent usability, cosmetic effects, and cosmetic durability.

[Evaluation of the Usability, Cosmetic Effects, and Cosmetic Durability of Powder Foundation]

Powder foundations having ingredients shown in Example 23 and Comparative Example 16 below were prepared, and the usability, cosmetic effects, and cosmetic durability of each powder foundation were evaluated.

(Producing Method)

A: Powdery ingredients were dispersed and mixed well.

B: Oily ingredients were mixed and dissolved well.

C: After B was added to A, the ingredients were mixed and pulverized, passed through a sieve, and then molded in a gold dish to obtain a powder foundation.

(Evaluation Method)

The method for evaluating the powder foundations was the same as in the case of the O/W emulsified foundations described above.

TABLE 7

|  | Ingredients | Example 23 | Comparative Example 16 |
|---|---|---|---|
| Powdery ingredients | Silicone-treated talc | Remainder (wt %) | Remainder (wt %) |
|  | Silicone-treated sericite | 16.0 | 25.0 |
|  | Silicone-treated mica | 10.0 | 10.0 |
|  | Silicone-treated spherical silica | 7.0 | 5.0 |
|  | Powder of Example 5 (titanium oxide) | 8.0 | — |
|  | Powder of Example 6 (yellow iron oxide) | 2.8 | — |
|  | Powder of Example 7 (red iron oxide) | 1.3 | — |
|  | Powder of Example 8 (black iron oxide) | 0.2 | — |
|  | Powder of Comparative Example 2 (titanium oxide) | — | 8.5 |
|  | Powder of Comparative Example 3 (yellow iron oxide) | — | 3.1 |
|  | Powder of Comparative Example 4 (red iron oxide) | — | 2.0 |
|  | Powder of Comparative Example 5 (black iron oxide) | — | 0.3 |

TABLE 7-continued

|  | Ingredients | Example 23 | Comparative Example 16 |
|---|---|---|---|
| Oily ingredients | 2-ethylhexyl p-methoxycinnamate | 3.0 | 3.0 |
|  | Glyceryl tri-2-ethylhexanoate | 2.0 | 2.0 |
|  | Dimethylpolysiloxane (20 cs) | 3.0 | 3.0 |
|  | Squalane | 3.0 | 3.0 |
|  | Sorbitan sesquioleate | 0.5 | 0.5 |
|  | Antibacterial agent | Appropriate amount | Appropriate amount |
|  | Antioxidant | Appropriate amount | Appropriate amount |
| Evaluation results | Usability | 4.5 | 3.5 |
|  | Cosmetic effects | 4.4 | 3.4 |
|  | Cosmetic durability | 4.2 | 3.6 |

The results of Table 7 show that the powder foundation comprising the powders of Examples 5 to 8 has excellent usability, cosmetic effects, and cosmetic durability.

[Evaluation of the Usability, Cosmetic Effects, and Cosmetic Durability of Oil-Based Solid Foundation]

Oil-based solid foundations having ingredients shown in Example 24 and Comparative Example 17 below were prepared, and the usability, cosmetic effects, and cosmetic durability of each oil-based solid foundation were evaluated.

(Producing Method)

A: Powdery ingredients were dispersed and mixed well.

B: Oily ingredients were mixed and dissolved well.

C: After B was added to A, the mixture was heated with a heating roller, poured into a gold dish, and then cooled and molded to obtain an oil-based solid foundation.

(Evaluation Method)

The method for evaluating the oil-based solid foundations was the same as in the case of the O/W emulsified foundations described above.

TABLE 8

|  | Ingredients | Example 24 | Comparative Example 17 |
|---|---|---|---|
| Oily ingredients | Polyglyceryl-2 triisostearate | 8.5 (wt %) | 8.5 (wt %) |
|  | Propylene glycol dicaprate | 10.0 | 10.0 |
|  | Dimethylpolysiloxane (20 cs) | 9.0 | 9.0 |
|  | Dimethicone/vinyl dimethicone crosspolymer | 5.0 | 5.0 |
|  | Petroleum jelly | 7.5 | 7.5 |
|  | Polyethylene wax | 4.0 | 4.0 |
|  | Candelilla wax | 1.5 | 1.5 |
|  | 2-ethylhexyl p-methoxycinnamate | 3.0 | 3.0 |
| Powdery ingredients | Alkylsilane-treated talc | Remainder | Remainder |
|  | Powder of Example 1 (titanium oxide) | 7.0 | — |
|  | Powder of Example 2 (yellow iron oxide) | 3.0 | — |
|  | Powder of Example 3 (red iron oxide) | 2.2 | — |
|  | Powder of Example 4 (black iron oxide) | 0.2 | — |
|  | Powder of Comparative Example 2 (titanium oxide) | — | 7.0 |
|  | Powder of Comparative Example 3 (yellow iron oxide) | — | 3.0 |
|  | Powder of Comparative Example 4 (red iron oxide) | — | 2.2 |
|  | Powder of Comparative Example 5 (black iron oxide) | — | 0.2 |

TABLE 8-continued

| Ingredients | | Example 24 | Comparative Example 17 |
|---|---|---|---|
| | Preservative | Appropriate amount | Appropriate amount |
| Evaluation results | Usability | 4.3 | 3.7 |
| | Cosmetic effects | 4.5 | 3.8 |
| | Cosmetic durability | 4.4 | 3.3 |

The results of Table 8 show that the oil-based solid foundation comprising the powders of Examples 1 to 4 has excellent usability, cosmetic effects, and cosmetic durability.
[Evaluation of the Usability, Cosmetic Effects, and Cosmetic Durability of Water-Based Oshiroi Face Powder]

Water-based oshiroi face powders having ingredients shown in Example 25 and Comparative Example 18 below were prepared, and the usability, cosmetic effects, and cosmetic durability of each water-based oshiroi face powder were evaluated.
(Producing Method)
A: Powdery ingredients were mixed well.
B: Water layer ingredients were mixed and dissolved.
C: After A was added to B, the mixture was stirred well to obtain a water-based oshiroi face powder.
(Evaluation Method)
The method for evaluating the water-based oshiroi face powders was the same as in the case of the O/W emulsified foundations described above.

TABLE 9

| | Ingredients | Example 25 | Comparative Example 18 |
|---|---|---|---|
| Powdery ingredients | Talc | 10.0 (wt %) | 10.0 (wt %) |
| | Boron nitride | 3.0 | 3.0 |
| | Synthetic mica | 3.5 | 3.5 |
| | Powder of Example 5 (titanium oxide) | 3.0 | — |
| | Powder of Comparative Example 1 (titanium oxide) | — | 3.0 |
| | Polyurethane powder | 5.0 | — |
| Water layer ingredients | BG | 5.0 | 5.0 |
| | Glycerin | 5.0 | 5.0 |
| | Ethanol | 5.0 | 5.0 |
| | EDTA 2Na | 0.2 | 0.2 |
| | Phenoxyethanol | 0.3 | 0.3 |
| | SEPINOV P88 | 0.2 | 0.2 |
| | Ion exchange water | Remainder | Remainder |
| Evaluation results | Usability | 4.4 | 3.5 |
| | Cosmetic effects | 4.2 | 3.3 |
| | Cosmetic durability | 4.0 | 3.1 |

The results of Table 9 show that the water-based oshiroi face powder comprising the powder of Example 5 has excellent usability, cosmetic effects, and cosmetic durability.
[Evaluation of the Usability, Cosmetic Effects, and Cosmetic Durability of Water-Based Eyeshadow]

Water-based eyeshadows having ingredients shown in Example 26 and Comparative Example 19 below were prepared, and the usability, cosmetic effects, and cosmetic durability of each water-based eyeshadow were evaluated.
(Producing Method)
A: Powdery ingredients were mixed well.
B: Water layer ingredients were mixed and dissolved.
C: After A was added to B, the mixture was stirred well to obtain a water-based eyeshadow.
(Evaluation Method)
The method for evaluating the water-based eyeshadows was the same as in the case of the O/W emulsified foundations described above.

TABLE 10

| | Ingredients | Example 26 | Comparative Example 19 |
|---|---|---|---|
| Powdery ingredients | Talc | 5.0 (wt %) | 5.0 (wt %) |
| | Pearl pigment | 15.0 | 15.0 |
| | Powder of Example 6 (yellow iron oxide) | 0.8 | — |
| | Powder of Example 7 (red iron oxide) | 0.2 | — |
| | Powder of Example 8 (black iron oxide) | 0.1 | — |
| | Powder of Comparative Example 3 (yellow iron oxide) | — | 0.8 |
| | Powder of Comparative Example 4 (red iron oxide) | — | 0.2 |
| | Powder of Comparative Example 5 (black iron oxide) | — | 0.1 |
| | Polymethylsilsesquioxane | 4.0 | 4.0 |
| Water layer ingredients | BG | 5.0 | 5.0 |
| | Glycerin | 5.0 | 5.0 |
| | Ethanol | 5.0 | 5.0 |
| | EDTA 2Na | 0.2 | 0.2 |
| | Citric acid | 0.03 | 0.03 |
| | Sodium citrate | 0.12 | 0.12 |
| | Phenoxyethanol | 0.3 | 0.3 |
| | SEPIMAX ZEN | 0.2 | 0.2 |
| | Ion exchange water | Remainder | Remainder |
| Evaluation results | Usability | 4.5 | 2.5 |
| | Cosmetic effects | 4.3 | 3.0 |
| | Cosmetic durability | 4.5 | 3.4 |

The results of Table 10 show that the water-based eyeshadow comprising the powders of Examples 6 to 8 has excellent usability, cosmetic effects, and cosmetic durability.
[Evaluation of the Usability, Cosmetic Effects, and Cosmetic Durability of Water-Based Makeup Bases]

Water-based makeup bases having ingredients shown in Example 27 and Comparative Example 20 below were prepared, and the usability, cosmetic effects, and cosmetic durability of each water-based makeup base were evaluated.
(Producing Method)
A: Powdery ingredients were mixed well.
B: An water layer ingredient BG and the ingredients of A were mixed and processed with a roller.
C: After A was added to B, the mixture was stirred well to obtain a water-based makeup base.
(Evaluation Method)
The method for evaluating the water-based makeup bases was the same as in the case of the O/W emulsified foundations described above.

TABLE 11

| | Ingredients | Example 27 | Comparative Example 20 |
|---|---|---|---|
| Powdery ingredients | Silicone-treated talc | 7.0 (wt %) | 7.0 (wt %) |
| | Powder of Example 2 (yellow iron oxide) | 0.7 | — |
| | Powder of Example 3 (red iron oxide) | 0.3 | — |
| | Powder of Example 4 (black iron oxide) | 3.0 | — |
| | Powder of Comparative Example 3 (yellow iron oxide) | — | 0.7 |

TABLE 11-continued

|   | Ingredients | Example 27 | Comparative Example 20 |
|---|---|---|---|
|   | Powder of Comparative Example 4 (red iron oxide) | — | 0.3 |
|   | Powder of Comparative Example 5 (black iron oxide) | — | 3.0 |
| Water layer ingredients | BG | 10.0 | 10.0 |
|   | Glycerin | 5.0 | 5.0 |
|   | Ethanol | 9.0 | 9.0 |
|   | EDTA 2Na | 0.2 | 0.2 |
|   | Phenoxyethanol | 0.3 | 0.3 |
|   | Ion exchange water | Remainder | Remainder |
| Evaluation results | Usability | 4.3 | 3.2 |
|   | Cosmetic effects | 4.4 | 3.3 |
|   | Cosmetic durability | 4.1 | 3.2 |

The results of Table 11 show that the water-based makeup base comprising the powders of Examples 2 to 4 has excellent usability, cosmetic effects, and cosmetic durability.

[Evaluation of the Usability, Cosmetic Effects, and Cosmetic Durability of Lipsticks]

Lipsticks having ingredients shown in Example 28 and Comparative Example 21 below were prepared, and the usability, cosmetic effects, and cosmetic durability of each lipstick were evaluated.

(Producing Method)

A: Oil layer ingredients were mixed well.

B: Powdery ingredients were mixed with the ingredients of A, and the mixture was dispersed with a roller.

C: After B was added to A, the mixture was uniformly mixed.

D: The water layer ingredients were mixed and warmed.

E: After D was added to C, the mixture was emulsified to obtain a lipstick.

(Evaluation Method)

The method for evaluating the lipsticks was the same as in the case of the O/W emulsified foundations described above.

TABLE 12

|   | Ingredients | Example 28 | Comparative Example 21 |
|---|---|---|---|
| Oil layer ingredients | Dextrin palmitate/ethylhexanoate | 8.0 (wt %) | 8.0 (wt %) |
|   | Cetyl octanoate | 20.0 | 20.0 |
|   | PEG-10 Dimethicone | 3.0 | 3.0 |
|   | Decamethylcyclopentasiloxane | 40.0 | 40.0 |
| Powdery ingredients | Bentonite | 0.8 | 0.8 |
|   | Powder of Example 5 (titanium oxide) | 3.5 | — |
|   | Powder of Comparative Example 2 (titanium oxide) | — | 3.5 |
|   | Powder of Example 3 (red iron oxide) | 0.7 | — |
|   | Dimethylpolysiloxane-treated hydrophobic red iron oxide | — | 0.7 |
| Water layer ingredients | BG | 5.0 | 5.0 |
|   | Sodium chloride | 0.5 | 0.5 |
|   | Purified water | Remainder | Remainder |
| Evaluation results | Usability | 4.5 | 3.6 |
|   | Cosmetic effects | 4.2 | 3.4 |
|   | Cosmetic durability | 4.0 | 3.8 |

The results of Table 12 show that the lipstick comprising the powders of Examples 3 and 5 has excellent usability, cosmetic effects, and cosmetic durability.

[Evaluation of the Non-Stickiness, Non-Oiliness, and Comfortableness of Antiperspirant]

Antiperspirants having ingredients shown in Example 29 and Comparative Example 22 below were prepared, and the non-stickiness, non-oiliness, and comfortableness of each antiperspirant were evaluated.

(Producing Method)

A: Powdery ingredients were mixed well.

B: Water layer ingredients were mixed and dissolved.

C: After A was added to B, the ingredients were mixed to obtain an antiperspirant.

(Evaluation Method)

The method for evaluating the antiperspirants was the same as in the case of the O/W emulsified foundations described above, except that non-stickiness, non-oiliness, and comfortableness were evaluated. Talc was used as the inorganic powder in Comparative Example 22. This talc as the inorganic powder was untreated and did not have a hydrophobic-coat or a hydrophilic-coat.

TABLE 13

|   | Ingredients | Example 29 | Comparative Example 22 |
|---|---|---|---|
| Powdery ingredients | Powder of Example 16 (zinc oxide) | 2.5 (wt %) | — |
|   | Powder of Example 17 (talc) | 6.0 | — |
|   | Dimethicone-treated hydrophobic micro zinc oxide | — | 2.5 |
|   | Talc as inorganic powder | — | 6.0 |
|   | Silica beads | 5.0 | 5.0 |
| Water layer ingredients | Sodium chloride | 0.1 | 0.1 |
|   | Ethanol | 38.0 | 38.0 |
|   | BG | 2.0 | 2.0 |
|   | Polyoxyethylene sorbitan monolaurate | 0.2 | 0.2 |
|   | Phenoxyethanol | 0.3 | 0.3 |
|   | Ion exchange water | Remainder | Remainder |
| Evaluation results | Non-stickiness | 4.2 | 3.4 |
|   | Non-oiliness | 4.2 | 3.5 |
|   | Comfortableness | 4.3 | 3.0 |

The results of Table 13 show that the antiperspirant comprising the powders of Examples 16 and 17 does not have stickiness or oiliness and is comfortable to use.

[Evaluation of Non-stickiness, Combability, and Hair smoothness Provided by Hair Treatment Agents]

Hair treatment agents having ingredients shown in Example 30 and Comparative Example 23 below were prepared, and non-stickiness, combability, and hair smoothness offered by each hair treatment agent were evaluated. Non-sticky, combable, and smooth hair may also be described as shiny and silky.

(Producing Method)

A: Oil layer ingredients were heated and mixed.

B: Water layer ingredients were dispersed and mixed.

C: After B was added to A, the ingredients were mixed well to obtain a hair treatment agent.

(Evaluation Method)

The method for evaluating the hair treatment agents was the same as in the case of the O/W emulsified foundations described above, except that non-stickiness, combability, and hair smoothness were evaluated. Talc was used as the inorganic powder in Comparative Example 23. This talc as the inorganic powder was untreated and did not have a hydrophobic-coat or a hydrophilic-coat.

TABLE 14

| | Ingredients | Example 30 | Comparative Example 23 |
|---|---|---|---|
| Oil layer ingredients | Glycol distearate | 1.5 (wt %) | 1.5 (wt %) |
| | Liquid paraffin | 10.0 | 10.0 |
| | Squalane | 5.0 | 5.0 |
| | Stearyl alcohol | 1.5 | 1.5 |
| | Dimethylpolysiloxane (10 cs) | 3.5 | 3.5 |
| | Stearic acid | 5.0 | 5.0 |
| Water layer ingredients | Powder of Example 17 (talc) | 5.0 | — |
| | Talc as inorganic powder | — | 5.0 |
| | Polyoxyethylene (3) stearyl alcohol | 4.5 | 4.5 |
| | Polyoxyethylene (10) cetyl ether | 2.0 | 2.0 |
| | BG | 6.0 | 6.0 |
| | Preservative | Appropriate amount | Appropriate amount |
| | Purified water | Remainder | Remainder |
| Evaluation results | Does not give stickiness | 4.2 | 3.3 |
| | Combability | 4.2 | 3.5 |
| | Hair smoothness | 4.1 | 3.4 |

The results of Table 14 show that the hair treatment agent comprising the powder of Example 17 does not have stickiness and gives hair excellent combability and smoothness.

SUMMARY

As described, in the hydrophilic inorganic powder comprising an inorganic powder as a base material, a hydrophobic-coat that covers the surface of the inorganic powder, and a hydrophilic-coat that covers the hydrophobic-coat, good hydrophilicity and self-dispersibility can be achieved if a hydrophilic surfactant having a branched alkyl moiety in its molecule, such as polyoxyethylene (10) isostearyl ether, is used.

Such findings are particularly useful since the desired properties (usability, cosmetic effects, and cosmetic durability) may not be achieved when a hydrophobic inorganic powder is hydrophilized nonselectively with a nonionic surfactant, as indicated by Comparative Examples 11 and 13.

What is claimed is:

1. A hydrophilic inorganic powder, comprising:
an inorganic powder as a base material;
a hydrophobic-coat that covers the surface of the inorganic powder; and
a hydrophilic-coat that covers the hydrophobic-coat, wherein
ingredients of the hydrophilic-coat comprise both of a hydrophilic surfactant and a lipophilic surfactant, and
each of the hydrophilic surfactant and the lipophilic surfactant has a branched alkyl moiety in their molecules,
wherein the hydrophilic inorganic powder has self-dispersibility in water or an aqueous solvent.

2. The hydrophilic inorganic powder according to claim 1, wherein
the hydrophilic-coat is a nonionic surfactant,
the hydrophilic surfactant has a branched alkyl moiety of C12 to C20 in its molecule, and
the lipophilic surfactant has a branched alkyl moiety of C16 to C30 in its molecule.

3. The hydrophilic inorganic powder according to claim 2, wherein
the hydrophilic surfactant is at least one selected from the following group A, and
the lipophilic surfactant is at least one selected from the following group B,
Group A:
Polyoxyethylene (10) isostearyl ether;
Polyoxyethylene (20) glyceryl triisostearate;
Polyoxyethylene (12) isostearate;
Polyoxyethylene (8) glyceryl isostearate;
Polyoxyethylene (10) isocetyl ether; and
Polyoxyethylene (5) isostearyl ether;
Group B:
Polyglyceryl (2) diisostearate;
Sorbitan sesquiisostearate; and
Polyoxyethylene (5) phytosterol.

4. The hydrophilic inorganic powder according to claim 1, wherein the hydrophilic surfactant is polyoxyethylene (10) isostearyl ether.

5. The hydrophilic inorganic powder according to claim 1, wherein the ingredients of the hydrophobic-coat comprise at least one selected from dimethylpolysiloxane, disodium cocoyl glutamate, methyl hydrogen polysiloxane, stearic acid, silicone, and monoisostearyl sebacate.

6. A cosmetic preparation containing the hydrophilic inorganic powder according to claim 1.

7. The hydrophilic inorganic powder according to claim 2, wherein the hydrophilic surfactant is polyoxyethylene (10) isostearyl ether.

8. The hydrophilic inorganic powder according to claim 3, wherein the hydrophilic surfactant is polyoxyethylene (10) isostearyl ether.

9. The hydrophilic inorganic powder according to claim 2, wherein the ingredients of the hydrophobic-coat comprise at least one selected from dimethylpolysiloxane, disodium cocoyl glutamate, methyl hydrogen polysiloxane, stearic acid, silicone, and monoisostearyl sebacate.

10. The hydrophilic inorganic powder according to claim 3, wherein the ingredients of the hydrophobic-coat comprise at least one selected from dimethylpolysiloxane, disodium cocoyl glutamate, methyl hydrogen polysiloxane, stearic acid, silicone, and monoisostearyl sebacate.

11. The hydrophilic inorganic powder according to claim 4, wherein the ingredients of the hydrophobic-coat comprise at least one selected from dimethylpolysiloxane, disodium cocoyl glutamate, methyl hydrogen polysiloxane, stearic acid, silicone, and monoisostearyl sebacate.

12. A cosmetic preparation containing the hydrophilic inorganic powder according to claim 2.

13. A cosmetic preparation containing the hydrophilic inorganic powder according to claim 3.

14. A cosmetic preparation containing the hydrophilic inorganic powder according to claim 4.

15. A cosmetic preparation containing the hydrophilic inorganic powder according to claim 5.

* * * * *